US007313957B1

(12) United States Patent
Kuramori et al.

(10) Patent No.: US 7,313,957 B1
(45) Date of Patent: Jan. 1, 2008

(54) APPARATUS, METHOD AND PROGRAM FOR EVALUATING WORK CHARACTERISTIC

(75) Inventors: Akira Kuramori, Kanagawa (JP); Noritaka Koguchi, Kanagawa (JP); Masayoshi Kamijo, Nagano (JP); Tsugutake Sadoyama, Ibaraki (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 0 days.

(21) Appl. No.: 11/454,188

(22) Filed: Jun. 15, 2006

(51) Int. Cl.
*A61B 5/22* (2006.01)

(52) U.S. Cl. .................................... 73/379.01; 600/546

(58) Field of Classification Search ........... 73/379.012, 73/379.02; 600/546, 590
See application file for complete search history.

(56) References Cited

U.S. PATENT DOCUMENTS

| | | | | |
|---|---|---|---|---|
| 2005/0080350 A1* | 4/2005 | Kuramori et al. | ........... | 600/546 |
| 2005/0090757 A1* | 4/2005 | Kuramori et al. | ........... | 600/546 |
| 2005/0245838 A1* | 11/2005 | Kuramori et al. | ........... | 600/546 |
| 2005/0277843 A1* | 12/2005 | Kuramori et al. | ........... | 600/546 |

FOREIGN PATENT DOCUMENTS

| | | |
|---|---|---|
| EP | 1 516 587 A2 | 3/2005 |
| EP | 1 535 571 A1 | 6/2005 |
| JP | 2002-230699 | 8/2002 |
| JP | 2004-49623 | 2/2004 |

OTHER PUBLICATIONS

European Search Report by European Patent Office on Jan. 22, 2007.

M. Myrtek et al., "Physical, mental, emotional, and subjective workload components in train drivers", Ergonomics, 1994, vol. 37, No. 7, pp. 1195-1203.

Jun Tanaka et al., "Workload of Using a driver Assistance System", 2000 IEEE Intelligent Transportation Systems Conference Proceedings Dearborn (MI), USA, Oct. 1-3, 2000, pp. 382-386.

Kiparski et al., "[Assessment of Physical and Psychological Strain During the Climbing up of High Broadcasting Masts by Physiological Parameters]", International Archives of Occupational and Environmental Health, 1982, vol. 50, No. 3, 1982, pp. 237-244.

* cited by examiner

*Primary Examiner*—Jewel Thompson
(74) *Attorney, Agent, or Firm*—Knobbe Martens Olson & Bear LLP

(57) ABSTRACT

During a driving activity of an automobile, a work characteristic evaluating apparatus is provided for judging a factor (a physical work load or a mental load) of stress that a work activity places on the worker to evaluate a work characteristic. The work characteristic evaluating apparatus 1 comprises a masseter muscle myoelectric potential acqusition device 10 which measures and acquires myoelectric potential of a masseter muscle which moves independently of the driving activity of the driver, a work intensity acquisition device 20 which measures and acquires steering torque around the steering shaft as a work intensity of steering activity, a correlation calculating module 38 which computes a correlation between time-series data of the myoelectric potential of the masseter muscle and time-series data of the steering torque, and a judgment module 39 which judges whether the stress placed on the worker is caused by a physical work load or a mental load based on the correlation coefficient.

12 Claims, 3 Drawing Sheets

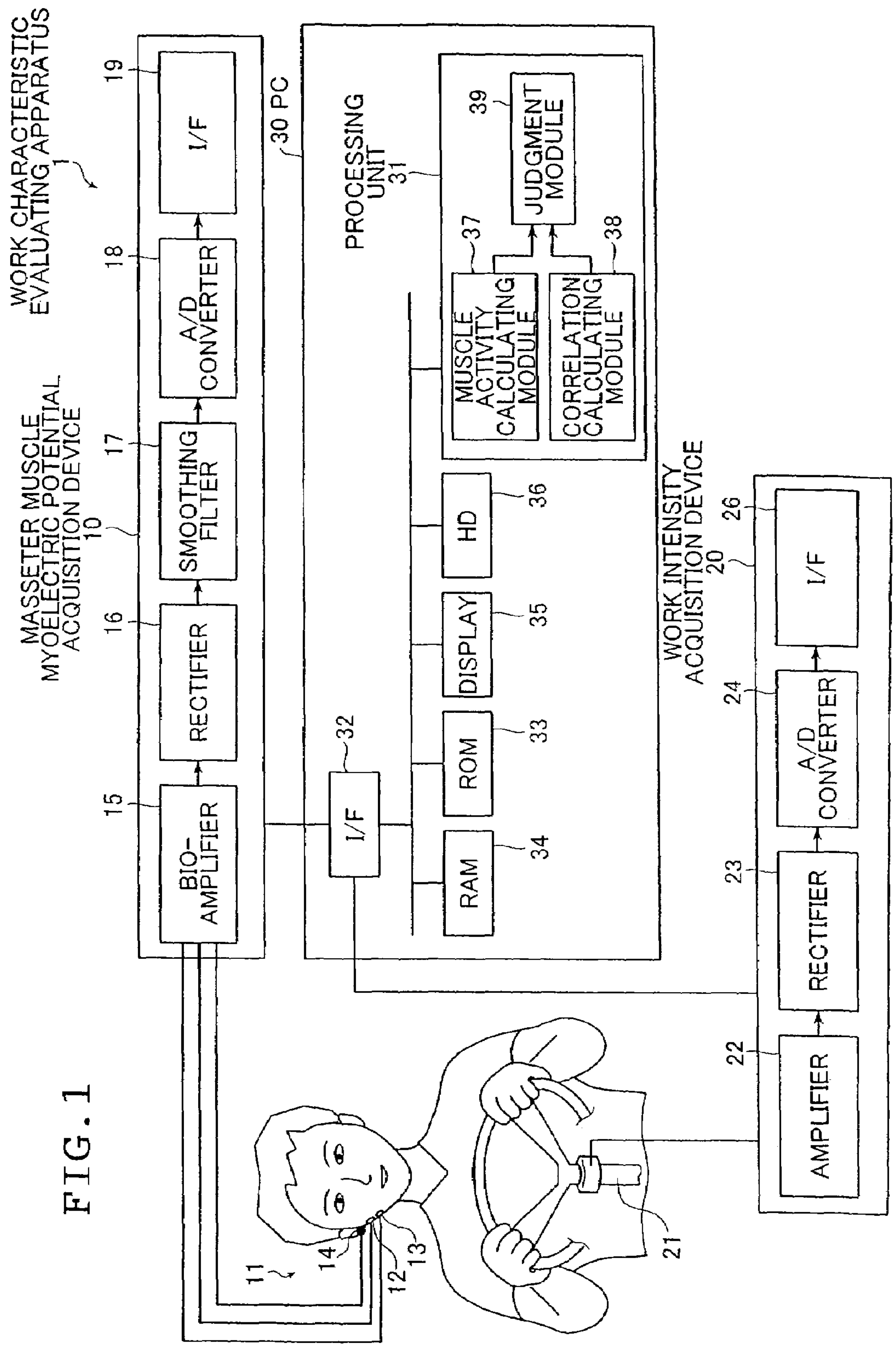
FIG. 1
WORK CHARACTERISTIC EVALUATING APPARATUS
1
MASSETER MUSCLE MYOELECTRIC POTENTIAL ACQUISITION DEVICE
10
BIO-AMPLIFIER
RECTIFIER
SMOOTHING FILTER
A/D CONVERTER
I/F
15
16
17
18
19
30 PC
PROCESSING UNIT
31
I/F
32
RAM
ROM
DISPLAY
HD
34
33
35
36
MUSCLE ACTIVITY CALCULATING MODULE
CORRELATION CALCULATING MODULE
JUDGMENT MODULE
37
38
39
WORK INTENSITY ACQUISITION DEVICE
20
AMPLIFIER
RECTIFIER
A/D CONVERTER
I/F
22
23
24
26
21
11
12
13
14

APPARATUS, METHOD AND PROGRAM FOR EVALUATING WORK CHARACTERISTIC

BACKGROUND OF THE INVENTION

1. Field of the Invention

The present invention relates to a work characteristic evaluating apparatus, a work characteristic evaluation method, and a program, for evaluating a work characteristic by judging a factor of stress that is placed on a worker through a work activity, in particular, a work characteristic evaluating apparatus, a work characteristic evaluating method, and a program, for judging a factor of stress that is placed on a driver through a vehicle driving activity.

2. Description of the Prior Art

Up to now, various technical developments have been made for automobiles to allow high-speed and safe driving. Various other techniques are still under study to allow a driver to comfortably drive an automobile.

In order to allow a comfortable drive, automobile manufacturers companies and the like are now studying a method of judging a degree of driving burden placed on a driver.

For example, as an example of the method of judging the driving burden on the driver who is driving an automobile, JP 2002-230699 A (hereinafter, referred to as Patent Document 1) discloses a method of judging a driving burden on a driver with good responsiveness based on a competitive state between a plurality of muscles used for a driving operation.

To be specific, a competitive value between muscles is calculated by multiplying a myoelectric potential of a biceps brachii muscle and that of a triceps brachii muscle. It is judged whether or not a driving burden is increased based on whether or not the calculated competitive value exceeds a predetermined threshold value.

JP 2004-49623 A (hereinafter, referred to as Patent Document 2) discloses a method of judging stress placed on a driver when the driver drives an automobile.

To be specific, a myoelectric signal of a masseter muscle is measured while the driver is driving. Based on the measured myoelectric signal, the stress placed on the driver is judged.

However, the method disclosed in Patent Document 1 is disadvantageous in that a driving burden (stress) to be judged caused by a physical work load and that caused by a mental load cannot be discriminated from each other. During the driving of an automobile, for example, there are cases where a great physical work load is placed by a steering operation for too small an assist rate of power steering of the automobile and where the mental load is placed by driving an unfamiliar automobile. The judgment cannot be made independently for each of the cases.

Similarly, even in Patent Document 2, the judgment of the degree of the driving burden cannot be made independently for the physical work load and the mental load.

BRIEF SUMMARY OF THE INVENTION

The present invention has an object to provide a work characteristic evaluating apparatus, a work characteristic evaluating method, and a program, for judging a factor of stress (physical work load or mental load) that is placed on a worker through a work activity, such as a driving activity of an automobile, and for enabling an evaluation of the work characteristic.

The present invention provides a work characteristic evaluating apparatus for judging a factor of stress that a work activity performed by a worker places on the worker to evaluate a work characteristic, the work characteristic evaluating apparatus including: a muscle activity acquisition section for obtaining information of a muscle activity in a muscle of the worker, which moves independently of the work activity performed by the worker; a work intensity measurement section for measuring a work intensity of the work activity performed by the worker; a computing section for obtaining a correlation between time-series data of the information of the muscle activity and time-series data of the work intensity; and a judgment section for judging whether the stress placed on the worker is caused by a physical work load of the work activity or a mental load of the work activity based on a degree of the correlation to evaluate the work characteristic.

It is preferred that the muscle activity acquisition section obtains a myoelectric potential indicating the muscle activity of the muscle through measurement.

Moreover, it is preferred that the judgment section evaluates the work characteristic by using a numerical value indicating an intensity of the myoelectric potential measured by the muscle activity acquisition section, and the degree of correlation obtained by the computing section.

It is preferred that the judgment section judges that a strain is present in a case that the numerical value indicating an intensity of the myoelectric potential exceeds a threshold value, and the judgment section judges that the stress is caused by a physical work load in a case that the degree of the correlation exceeds a predetermined value in addition to the former case.

It is preferred that the work intensity measurement section measures a physical quantity acting on a work subject. Alternatively, it is also preferred that the work intensity measurement section measures an activity of the muscle used for the work activity for a work intensity.

The work activity requires use of arms or legs and it is preferred that the muscle activity acquisition section uses a muscle activity of a muscle selected from the group consisting of a masseter muscle, a sternocleidomastoid muscle, a cowl muscle, and a temporal muscle, as the muscle activity of the muscle moving independently of the work activity.

The work activity is, for example, a driving activity of an automobile.

Further, the present invention provides a work characteristic evaluating method for judging a factor of stress that a work activity performed by a worker places on the worker to evaluate a work characteristic, the work characteristic evaluating method including the steps of: obtaining information of a muscle activity in a muscle of the worker, which moves independently of the work activity performed by the worker; measuring a work intensity of the work activity performed by the worker; obtaining a correlation between time-series data of the information of the muscle activity and time-series data of the work intensity; and judging whether the stress placed on the worker is caused by a physical work load of the work activity or a mental load of the work activity based on a degree of the correlation to evaluate the work characteristic.

It is preferred that a myoelectric potential indicating the muscle activity of the muscle through measurement is obtained as the information of the muscle activity. When the judgment is made, it is preferred that the work characteristic is evaluated by using a numerical value indicating an intensity of the measured myoelectric potential and the degree of the obtained correlation. When the judgment is made, a judgment that a strain is present is preferably made in a case that the numerical value indicating an intensity of the myoelectric potential exceeds a threshold value, and a judgment that the stress is caused by a physical work load is made in a case that the degree of the correlation exceeds a predetermined value in addition to the former case.

Further, the present invention provides a program for causing a computer to execute a process of judging a factor of stress that a work activity places on a worker to evaluate a work characteristic, the program including the procedures of: causing the computer to obtain time-series data of information of a muscle activity in a muscle of the worker, which moves independently of the work activity performed by the worker, and time-series data of a work intensity in the work activity performed by the worker; causing a computing unit of the computer to correlate the obtained time-series data of the information of the muscle activity and the obtained time-series data of the work intensity; and causing the computing unit of the computer to judge whether the stress placed on the worker is caused by a physical work load of the work activity or a mental load of the work activity based on a degree of the correlation to evaluate the work characteristic.

It is preferred that the program causes the computer to obtain a myoelectric potential indicating the muscle activity of the muscle through measurement as the time-series data of information of a muscle activity. When the judgment is made, the program is preferred to cause the computing unit to evaluate the work characteristic by using a numerical value indicating an intensity of the measured myoelectric potential and the degree of the obtained correlation. When the judgment is made, the program is preferred to cause the computing unit to judge that a strain is present in a case that the numerical value indicating an intensity of the myoelectric potential exceeds a threshold value, and the program is preferred to cause the computing unit to judge that the stress is caused by a physical work load in a case that the degree of the correlation exceeds a predetermined value in addition to the former case.

In the present invention, the correlation between the time-series data of the myoelectric potential in the muscle of the worker, which moves independently of the work activity performed by the worker, and the time-series data of the work intensity of the work activity performed by the worker is obtained. It is judged whether the stress placed on the worker is caused by the physical work load of the work activity or the mental load of the work activity based on the degree of correlation. Accordingly, the factor of the stress that the work activity places on the worker can be judged.

BRIEF DESCRIPTION OF THE DRAWINGS

In the accompanying drawings:

FIG. 1 is a block diagram for explaining a configuration of a work characteristic evaluating apparatus according to the present invention;

DESCRIPTION OF THE PREFERRED EMBODIMENT

Hereinafter, a work characteristic evaluating apparatus, a work characteristic evaluating method, and a program therefor, according to the present invention will be described in detail based on the embodiment illustrated in the accompanying drawings.

Figure 2:
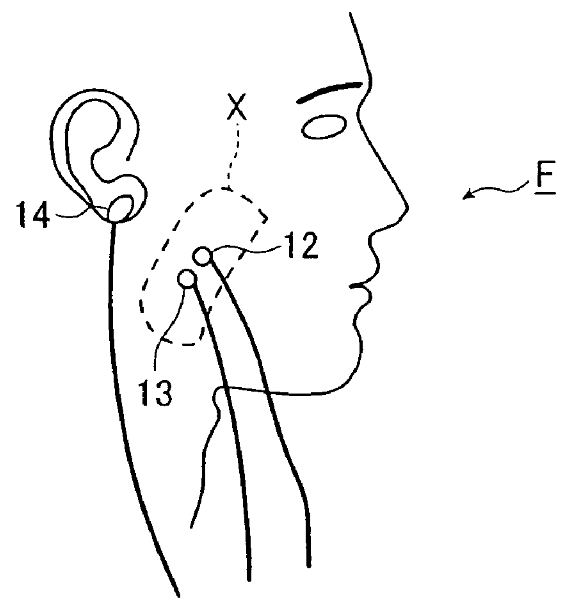
FIG. 2 is a view showing an example of how to attach electrodes for obtaining a myoelectric signal to measure a "strain" during a work activity according to the present invention.

FIG. 1 is a block diagram for explaining a configuration of a work characteristic evaluating apparatus according to the present invention. FIG. 2 is a view showing an example of attachment of electrodes for obtaining a signal of a myoelectric potential (myoelectric signal) to measure a "strain" during a work activity in an embodiment of the present invention.

In FIG. 1, a work characteristic evaluating apparatus 1 includes: a masseter muscle myoelectric potential acquisition device 10 for obtaining a myoelectric potential generated by a muscle activity of a masseter muscle of a driver; a work intensity acquisition device 20 for measuring, as a work intensity, a steering torque when the driver steers a wheel; and a personal computer (PC) 30 for judging whether a driving burden in a driving activity of an automobile performed by the driver is caused by a physical driving activity load or a mental load based on the myoelectric signal obtained by the masseter muscle myoelectric potential acquisition device 10 and the work intensity obtained by the work intensity acquisition device 12.

The masseter muscle myoelectric potential acquisition device 10 uses a sensor 11 to detect a myoelectric potential indicating an activity of a masseter muscle. The sensor 11 includes electrodes 12 and 13 placed about 5 mm apart and an earth electrode 14 for establishing a reference potential. As shown in FIG. 2, the electrodes 12 and 13 are attached to a skin of the upper part of a masseter muscle X (indicated by a broken line) of a face F, and the earth electrode 14 is attached to an earlobe. The earth electrode 14 is grounded through the masseter muscle myoelectric potential acquisition device 10.

The masseter muscle is a large muscle present on either side of the face, which moves independently of a driving activity performed by the driver. The masseter muscle is called a masticatory muscle together with a temporal muscle, and works on the actions of closing jaws, e.g., chewing and speaking actions. Accordingly, the masseter muscle does not normally move during a work activity such as the driving of an automobile performed by using muscles in arms, legs, and the like. If stress develops in a driver and causes the driver to tense all over, however, a "strain" also develops in the masseter muscle to move the masseter muscle. The masseter muscle myoelectric potential acquisition device 10 measures a myoelectric potential of the masseter muscle when the "strain" is developed.

The masseter muscle myoelectric potential acquisition device 10 includes: a bio-amplifier 15 which amplifies a myoelectric signal from each of the electrodes 12 and 13; a rectifier 16 which rectifies the myoelectric signal having an AC waveform to a myoelectric signal having a DC waveform; a smoothing filter 17 which removes noise from within the myoelectric signal; an A/D converter 18 which converts the myoelectric signal as an analog signal to digital signal data; and an interface (I/F) 19 which controls the transmission and reception of data to/from the PC 30.

In this embodiment, the myoelectric potential is used as information of a muscle activity. However, the present invention is not limited thereto. For example, an acceleration sensor may be provided on a muscle to measure a muscle sound. The muscle sound is a kind of pressure wave resulting from the lateral expansion of the diameter of a muscle fiber when the muscle fiber contracts. The muscle sound is a signal reflecting a mechanical activity of the muscle.

In the masseter muscle myoelectric potential acquisition device 10, when a driver undergoes stress from steering for a right turn, a left turn, or the like during the driving of an automobile (during a work activity) and tenses up all over to develop a "strain" in the masseter muscle, the myoelectric signal resulting from the "strain" in the masseter muscle is input from each of the electrodes 12 and 13. Then, after the myoelectric signal is amplified by the bio-amplifier 15, rectified by the rectifier 16, and further subjected to noise removal by the smoothing filter 17, the myoelectric signal is converted to a digital signal by the A/D converter 18. Time-series data of the digitized myoelectric potential is transferred to the PC 30 via the I/F 19.

The work intensity acquisition device 20 measures a work intensity of a driving activity performed by the driver and obtains, as the work intensity, a steering torque measured by a steering torque meter 21 attached to a steering shaft of an automobile. In the work intensity acquisition device 20, after a time-series signal of the steering torque is amplified by an amplifier 22 and is subjected to full-wave rectification by a rectifier 23, the time-series signal is converted to a digital signal by the A/D converter 24. Time-series data of the digitized steering torque is transmitted to the PC 30 via the I/F 26. It is preferred that a sampling clock frequency of the A/D converter 24 is the same as that of the A/D converter 18 in view of the computation of a correlation coefficient described below.

The PC 30 is a judging/evaluating device which judges the degree of stress placed on a driver during the driving and a factor of the stress to evaluate a work characteristic based on the time-series data of the myoelectric potential transmitted from the masseter muscle myoelectric potential acquisition device 10.

The PC 30 primarily includes: a processing unit 31 which invokes various program modules as required to perform a processing; an interface (I/F) 32 which controls the transmission and reception of data to/from the masseter muscle myoelectric potential acquisition device 10; a ROM 33 and a RAM 34, each storing various programs executed by the processing unit 31 and various data; a display 35 which displays the result of judgment and the like; and a hard disk (HD) 36 which stores the myoelectric signal, various programs, and various data transmitted from the masseter muscle myoelectric potential acquisition device 10. The processing unit 31, the I/F 32, the ROM 33, the RAM 34, the display 35, and the HD 36 are connected to each other through buses.

The processing unit 31 executes the evaluation of a work characteristic by invoking: a muscle activity calculating module 37 which calculates an intensity of the myoelectric potential indicating the degree of a muscle activity of the masseter muscle (a root mean square (RMS) value or an integral value (integrated electromyogram (IEMG)) over a given period of time); a correlation calculating module 38 which calculates a correlation coefficient between the time-series data of the steering torque obtained by the work intensity acquisition device 20 and the time-series data of the myoelectric potential of the masseter muscle; and a judgment module 39 which judges a factor of the stress based on the intensity of the myoelectric potential and the correlation coefficient to evaluate a work characteristic.

Each of these modules may be stored in any of the ROM 33, the RAM 34, and the HD 36. The individual modules may be stored separately. The modules may also be stored in a CD-ROM or any of other storage media (not shown).

The muscle activity calculating module 37 receives an input of the time-series data of the myoelectric potential transferred in real time from the masseter muscle myoelectric potential acquisition device 10 to temporarily store the received time-series data in the RAM 34 or the HD 36. The muscle activity calculating module 37 also uses the time-series data invoked from the RAM 34 or the HD 36 to calculate a parameter serving as an index for the judgment of stress. The muscle activity calculating module 37 defines, for example, a function for calculating the RMS value to perform a process of calculating the RMS value for the time-series data of the myoelectric potential which is input.

The correlation calculating module 38 calculates a correlation coefficient between the time-series data of the myoelectric potential within a predetermined time period from the masseter muscle myoelectric potential acquisition device 10 and the time-series data of the steering torque within the predetermined time period from the work intensity acquisition device 20. The myoelectric potential indicates a "strain" developed in the masseter muscle, and corresponds to the stress placed on the driver. Therefore, a correlation coefficient between the time-series data of the myoelectric potential indicating the stress and the time-series data of the steering torque indicating the work intensity is obtained. As a result, when the degree of correlation is high, the stress can be judged to be caused by a physical work load. On the other hand, when the degree of correlation is low, the stress can be judged to be caused by a mental load.

The judgment module 39 judges and evaluates a characteristic as a work based on the value such as the RMS or the IEMG calculated by the muscle activity calculating module 37 and the correlation coefficient calculated by the correlation calculating module 38.

Figure 3:
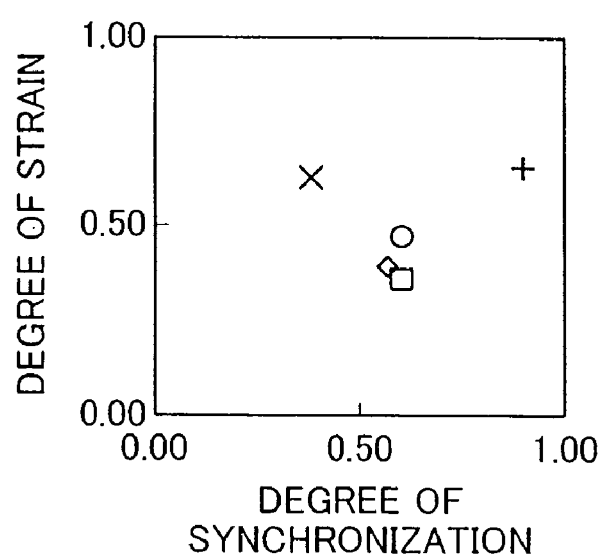
FIG. 3 is a view showing an example of a characteristic map created to judge and evaluate a characteristic of a work in the work characteristic evaluating apparatus according to the present invention.

FIG. 3 is an example of a characteristic map created to judge and evaluate a characteristic as a work activity.

In FIG. 3, a "degree of synchronization" on the abscissa axis indicates a value of the correlation coefficient, whereas a "degree of strain" on the ordinate axis indicates a value obtained by normalizing the RMS value. The RMS value is normalized in the following manner. The RMS is calculated by measuring in advance a waveform of the maximum contraction potential of the masseter muscle when the driver clenches the back teeth as hard as he (she) can to calculate the RMS value. Then, the calculated RMS value is used for normalization. On the characteristic map, as the "degree of strain" becomes higher, the stress that the driver undergoes is greater. On the other hand, as the "degree of synchronization" becomes higher, the physical work load on the driver exceeds the mental load by a larger difference.

In FIG. 3, the results (Examples 1 to 5) of when drivers drive automobiles, each with a different type of tire fitted thereto, are overwritten on the characteristic map as described above. The results are obtained when a lane change is made at the speed of 100 km/hour. Each of the results corresponds to an average value of three drivers.

Example 4('X' mark) has the "degree of strain" as high as that of Example 5(+mark) as compared with Examples 1 to 3('○', '◇', '□' marks). However, the "degree of synchronization" of Example 4('X' mark) is lower than those of Examples 1 to 3('○', '◇', '□'), marks). On the other hand, the "degree of synchronization" of Example 5('+' mark) is higher than those of Examples 1 to 3('○', '◇', '□' marks).

In view of the above results, driving activities in Example 4('X' mark) and that in Example 5('+' mark) place the same degree of stress on the driver. However, a factor of the stress in Example 4('X' mark) can be judged and evaluated as a mental load, whereas that in Example 5('+' mark) can be judged and evaluated as a physical work load.

The PC 30 as described above functions by invoking the following program from the ROM 33, the HD 36, or the like. To be specific, the program includes the procedures of: causing a computer to obtain the time-series data of the myoelectric potential of the muscle of the worker, which moves independently of the work performed by the worker, and the time-series data of the work intensity in the work activity performed by the worker; causing a computing unit of the computer to calculate a correlation between the obtained time-series data of the myoelectric potential and the time-series data of the work intensity; and causing the computing unit of the computer to judge whether the stress placed on the worker is caused by a physical work load of the work activity or a mental load of the work activity based on the calculated degree of correlation to evaluate a work characteristic.

The work characteristic evaluating apparatus 1 is configured as described above.

Although the steering operation of an automobile is regarded as the work activity and the steering torque is used as the work intensity in this embodiment, a steering work rate obtained by multiplying the steering torque by a steering angular velocity may be used in place of the steering torque. When the work activity corresponds to a gear shift operation, an operating force of a shift lever may be suitably used. When pedals such as an accelerator, a brake, or a clutch are operated with a foot, a leg-power placed on the pedal may be suitably used.

The work activity in the present invention is not limited to the driving of an automobile. As the work intensity, an intensity such as a measurable work force, work horsepower (energy), or a work activity work rate can be used. The work force is detected by, for example, using a load cell as a sensor. The work force is also detected by a pressure-sensitive glove or a floor reaction force meter. For the work horsepower or the work activity work rate, in addition to the measurement of the work force by using the load cell or the like, a displacement of a work site is measured by a displacement sensor or the like.

Moreover, in the present invention, the muscle of the worker, which moves independently of the work activity performed by the worker, may be any muscle which does not move or only slightly moves in a relaxed state during the work activity, and which does not correspond to an agonist muscle or an antagonist muscle of the work activity. As examples of such muscles, besides the masseter muscle, a temporal muscle of a head, a sternocleidomastoid muscle of a neck, and a cowl muscle of a shoulder can be given. A myoelectric signal of one of the above-mentioned muscles can also be used.

Further, although the measurable work force, work horsepower, or work activity work rate exerted on a work subject is used as the work intensity in this embodiment, the myoelectric potential of an agonist muscle or an antagonist muscle of the worker in the work activity during the work activity may be a target to be measured to be used for calculating the work intensity. For example, in the case of a work activity using the arms, a myoelectric potential of a biceps brachii muscle or a triceps brachii muscle serving as the agonist muscle of the arm, an extensor muscle or a flexor muscle of a forearm, or a deltoid muscle or a cowl muscle of the shoulder may be measured. In particular, when the work activity is performed on a plurality of work subjects, it is more preferable to measure the myoelectric potential of the agonist muscle of the worker than to measure an operating force, a torque, a displacement, an angle, or the like on each of the work subjects for simplicity. Such a myoelectric potential can be measured by attaching a pair of electrodes on a part of the muscle to be measured and using a myoelectric potential acquisition device having the same configuration as that of the masseter muscle myoelectric potential acquisition device 10. Such a work activity is frequently performed in the actual field of work, and therefore the above-described means is effective.

Figure 4:
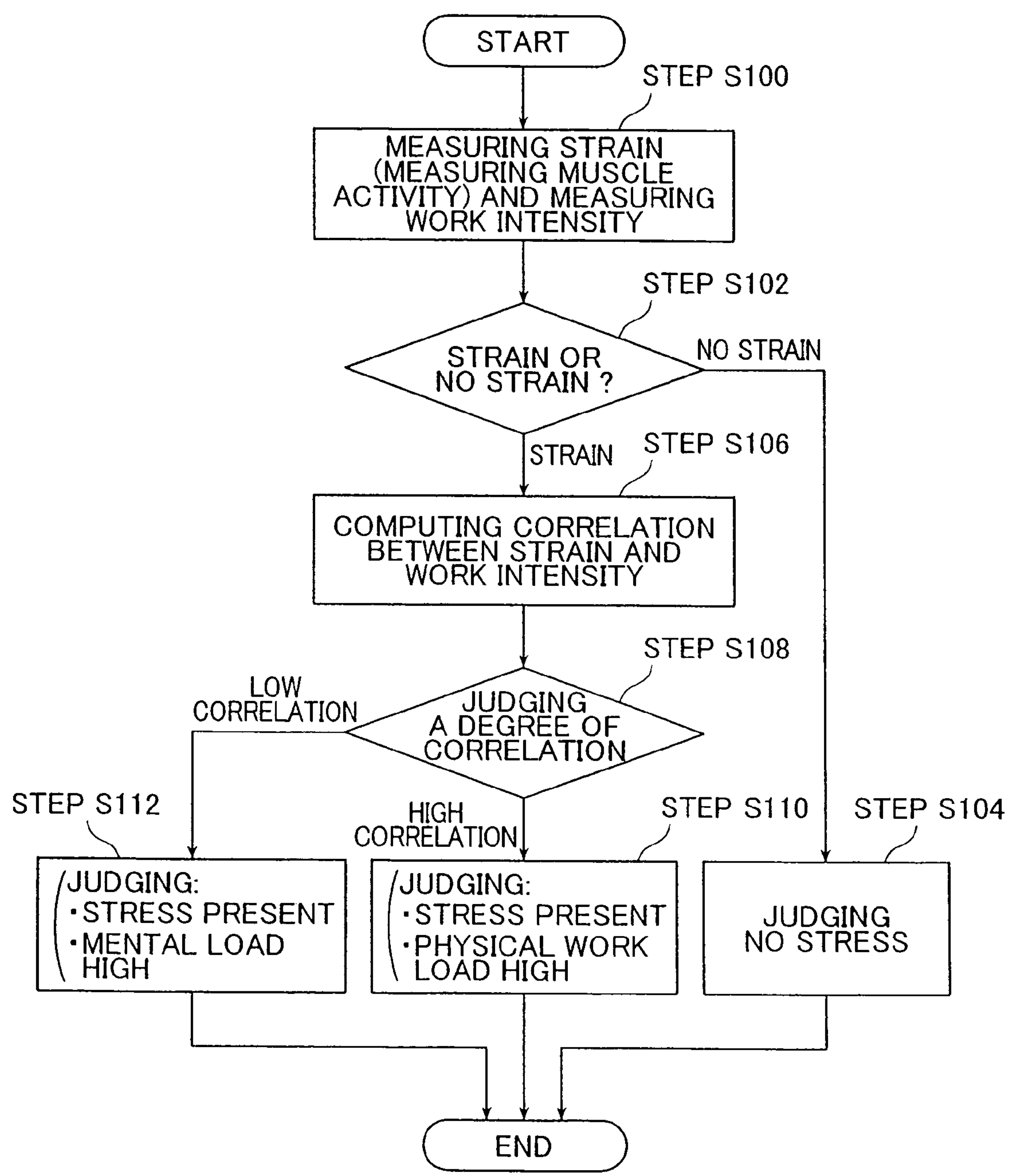
FIG. 4 is a flowchart showing a flow of a work characteristic evaluating method carried out in the work characteristic evaluating apparatus according to the present invention.

FIG. 4 is a flowchart showing the flow of a work characteristic evaluating method performed in the work characteristic evaluating apparatus 1.

First, the masseter muscle myoelectric potential acquisition device 10 is used to measure the myoelectric potential of the masseter muscle as a "strain", thereby obtaining time-series data of the myoelectric potential. In the work intensity acquisition device 20, the steering torque acting about the steering shaft is measured as the work intensity to obtain the time-series data of the steering torque (Step S100).

Based on the time-series data of the myoelectric potential, the RMS value within a predetermined time range is calculated as the degree of "strain" in the muscle activity calculating module 37. The calculated RMS value is divided by the pre-measured RMS value at the maximum contraction potential, thereby to be represented as the "degree of strain" shown in FIG. 3.

Next, the "degree of strain" is compared with a predetermined value to judge whether or not the "strain" is present (Step S102). For example, when the "degree of strain" is 0.5 or lower, it is judged that there is no "strain". It is therefore judged that no stress is developed in the work activity (Step S104).

In Step S102, for example, when the "degree of strain" exceeds 0.5, it is judged that the "strain" is present. In this case, a correlation coefficient between the time-series data of the steering torque obtained as the work intensity and the time-series data of the myoelectric potential of the masseter muscle is calculated (Step S106). To be specific, a correlation coefficient between the two time-series data within a preset time range is calculated.

As the degree of correlation in the present invention, besides the correlation coefficient between the two time-series data obtained at the same time, a cross-correlation function of two time-series data may be calculated and the maximum value of the cross-correlation function can be used. This is because the myoelectric potential indicating the "strain" has a correlation of a given time lag in some cases with respect to the work intensity.

Next, by using the calculated correlation coefficient, the magnitude of the correlation between the work intensity and the "strain" is judged (Step S108). The magnitude of the correlation is compared with a preset value. In this comparison, when the correlation coefficient is equal to or larger than the set value, the correlation between the "strain" and the work intensity is high. Therefore, it is judged that the work activity places stress on the driver and the stress is caused by a physical work load (Step S110). On the other hand, when the correlation coefficient is smaller than the set value, the correlation between the "strain" and the work intensity is low. Therefore, it is judged that the work activity places stress on the driver and the stress is caused by a mental load (Step S112).

As described above, the information indicating whether or not the driving places stress on the driver is given. Together with the information, a factor of the stress is judged to be either mental or physical when the stress is placed on the driver. In this manner, the work characteristic can be evaluated.

Although the work characteristic evaluating apparatus, the work characteristic evaluating method, and the program therefor have been described above in detail, the present invention is not limited to the above-described embodiment. It is apparent that various modifications and changes are possible without departing from the scope of the present invention.

The invention claimed is:

1. A work characteristic evaluating apparatus for judging a factor of stress that a work activity performed by a worker places on the worker to evaluate a work characteristic, the work characteristic evaluating apparatus including:

a muscle activity acquisition section for obtaining information of a muscle activity in a muscle of the worker, which moves independently of the work activity performed by the worker;

a work intensity measurement section for measuring a work intensity of the work activity performed by the worker;

a computing section for obtaining a correlation between time-series data of the information of the muscle activity and time-series data of the work intensity; and a judgment section for judging whether the stress placed on the worker is caused by a physical work load of the work activity or a mental load of the work activity based on a degree of the correlation to evaluate the work characteristic.

2. The work characteristic evaluating apparatus according to claim 1, wherein the muscle activity acquisition section obtains a myoelectric potential indicating the muscle activity of the muscle through measurement.

3. The work characteristic evaluating apparatus according to claim 2, wherein the judgment section evaluates the work characteristic by using a numerical value indicating an intensity of the myoelectric potential measured by the muscle activity acquisition section, and the degree of the correlation obtained by the computing section.

4. The work characteristic evaluating apparatus according to claim 3, wherein the judgment section judges that a strain is present in a case that the numerical value indicating an intensity of the myoelectric potential exceeds a threshold value, and the judgment section judges that the stress is caused by a physical work load in a case that the degree of the correlation exceeds a predetermined value in addition to the former case.

5. The work characteristic evaluating apparatus according to claim 4, wherein the work intensity measurement section measures a physical quantity acting on a work subject.

6. The work characteristic evaluating apparatus according to claim 1, wherein the work intensity measurement section measures an activity of the muscle used for the work activity for a work intensity.

7. The work characteristic evaluating apparatus according to claim 1, wherein the work activity requires use of arms or legs and the muscle activity acquisition section uses a muscle activity of a muscle selected from the group consisting of a masseter muscle, a sternocleidomastoid muscle, a cowl muscle, and a temporal muscle, as the muscle activity of the muscle moving independently of the work activity.

8. The work characteristic evaluating apparatus according to claim 1, wherein the work activity is a driving activity of an automobile.

9. A work characteristic evaluating method for judging a factor of stress that a work activity performed by a worker places on the worker to evaluate a work characteristic, the work characteristic evaluating method including the steps of:

obtaining information of a muscle activity in a muscle of the worker, which moves independently of the work activity performed by the worker;

measuring a work intensity of the work activity performed by the worker;

obtaining a correlation between time-series data of the information of the muscle activity and time-series data of the work intensity; and judging whether the stress placed on the worker is caused by a physical work load of the work activity or a mental load of the work activity based on a degree of the correlation to evaluate the work characteristic.

10. The work characteristic evaluating method according to claim 9, wherein a myoelectric potential indicating the muscle activity of the muscle is obtained through measurement as the information of the muscle activity.

11. The work characteristic evaluating method according to claim 10, wherein the work characteristic is evaluated by using a numerical value indicating an intensity of the measured myoelectric potential and the degree of the obtained correlation.

12. The work characteristic evaluating method according to claim 11, wherein a judgment that a strain is present is made in a case that the numerical value indicating an intensity of the myoelectric potential exceeds a threshold value, and a judgment that the stress is caused by a physical work load is made in a case that the degree of the correlation exceeds a predetermined value in addition to the former case in the step of the judging.

* * * * *

UNITED STATES PATENT AND TRADEMARK OFFICE

CERTIFICATE OF CORRECTION

PATENT NO. : 7,313,957 B1
APPLICATION NO. : 11/454188
DATED : January 1, 2008
INVENTOR(S) : Kuramori et al.

It is certified that error appears in the above-identified patent and that said Letters Patent is hereby corrected as shown below:

| **Column** | **Line** | |
|---|---|---|
| First Page Col. 2 (Abstract) | 6 | Delete “acqusition” and insert -- acquisition --, therefor. |
| 6 | 65 | Delete “5(+mark)” and insert -- 5(‘+’mark) --, therefor. |
| 7 | 1 | Delete “‘□’),” and insert -- ‘□’ --, therefor. |

Signed and Sealed this

Eleventh Day of November, 2008

JON W. DUDAS
*Director of the United States Patent and Trademark Office*